(12) United States Patent
Kawanishi

(10) Patent No.: US 7,450,980 B2
(45) Date of Patent: Nov. 11, 2008

(54) INTRACORPOREAL SUBSTANCE MEASURING ASSEMBLY

(75) Inventor: Tetsuro Kawanishi, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 554 days.

(21) Appl. No.: 11/089,329

(22) Filed: Mar. 25, 2005

(65) Prior Publication Data
US 2005/0221277 A1 Oct. 6, 2005

(30) Foreign Application Priority Data
Mar. 31, 2004 (JP) .............................. 2004-107653

(51) Int. Cl.
*A61B 5/1455* (2006.01)
(52) U.S. Cl. ...................................... 600/317; 600/310
(58) Field of Classification Search ................. 600/310, 600/316, 317
See application file for complete search history.

(56) References Cited

U.S. PATENT DOCUMENTS

| 4,253,466 | A | 3/1981 | Hartlaub et al. |
| 4,550,731 | A | 11/1985 | Batina et al. |
| 5,137,833 | A | 8/1992 | Russell |
| 5,503,770 | A | 4/1996 | James et al. |
| 5,628,310 | A | 5/1997 | Rao et al. |
| 6,002,954 | A | 12/1999 | Van Antwerp et al. |
| 6,256,522 | B1 * | 7/2001 | Schultz ........................ 600/317 |
| 6,287,639 | B1 * | 9/2001 | Schmidt et al. ............. 427/387 |
| 6,304,766 | B1 | 10/2001 | Colvin, Jr. |
| 6,330,464 | B1 | 12/2001 | Colvin, Jr. et al. |
| 6,454,710 | B1 * | 9/2002 | Ballerstadt et al. .......... 600/365 |
| 6,682,938 | B1 | 1/2004 | Satcher, Jr. et al. |
| 6,794,195 | B2 | 9/2004 | Colvin, Jr. |
| 2004/0054385 | A1 * | 3/2004 | Lesho ........................ 607/60 |

FOREIGN PATENT DOCUMENTS

WO WO 01/20334 A 3/2001

OTHER PUBLICATIONS

European Search Report issued Jul. 25, 2005 in corresponding EP Application 05006888.1 - 2305.

* cited by examiner

*Primary Examiner*—Eric F. Winakur
*Assistant Examiner*—Etsub D Berhanu
(74) *Attorney, Agent, or Firm*—Buchanan Ingersoll & Rooney PC

(57) ABSTRACT

An intracorporeal substance measuring assembly to be provided in an embedded-type substance sensor for detecting and measuring an intercorporeal analyte includes: a detection layer containing at least one fluorescent indicator for generating fluorescence according to the concentration of the analyte; and an optical separation layer which is provided on the detection layer, is optically opaque, permits the analyte to penetrate therethrough, and prevents the penetration therethrough of at least one of living body substances possibly deteriorating the detection layer and/or obstructing the fluorescence.

11 Claims, 7 Drawing Sheets

INTRACORPOREAL SUBSTANCE MEASURING ASSEMBLY

BACKGROUND OF THE INVENTION

1. Field of the Invention

The present invention relates to an intracorporeal substance measuring assembly provided in an embedded type substance sensor for detecting and measuring an intracorporeal analyte, a method of producing the intracorporeal substance measuring assembly, and an embedded type substance sensor using the intracorporeal substance measuring assembly.

2. Description of the Prior Art

Embedded-in-body type sensors are useful for observation of the proceeding of a disease or for monitoring a therapeutic effect in various diseases, and constitute one of the fields which have been actively researched in recent years. Particularly, in treatment of diabetes, blood sugar control based on continuous blood sugar measurement is said to contribute to the retarding of progress of a disease or to a reduction in morbidity of complications.

Many of diabetic patients at present are making it a practice to draw a blood sample by puncturing a finger or the like, to supply the blood sample to a blood sugar meter, and are to read the measured value, for self-control of blood sugar. Such a method, however, has problems in view of pain to the patient and of easiness; the measurement is limited to several times a day, and it is difficult at present to frequently measure the variation in the blood sugar and to grasp the tendency of the variation. From these grounds, it is considered that an embedded type continuous blood sugar meter is highly useful.

As an embedded-in-body type sensor, an apparatus with transmission of signals to and from an instrument embedded in a living body on a wireless basis has been disclosed (refer to U.S. Pat. Nos. 4,550,731 and 4,253,466). According to this technology, a detection device (sensor) having an indicator layer of which the fluorescence property is varied through reaction with glucose reversibly is embedded in a living body, the glucose concentration is measured from the variation in fluorescence amount, and the data is led out to the exterior of the body by way of electromagnetic waves or the like.

In addition, as a material which can be used for the indicator of the detection device, there has been proposed one in which a fluorescent substance capable of reversible coupling with glucose, such as phenylboronic acid, is covalently bonded to polystyrene (refer to U.S. Pat. No. 5,137,833).

Besides, while various saccharide components are present in a living body component, a fluorescent substance capable of specific and reversible coupling with glucose has been proposed (refer to U.S. Pat. No. 5,503,770).

However, these conventional embedded-in-body type sensors have the problems that the substance (indicator substance) for generating fluorescence upon contact with an analyte is deteriorated during use and cannot endure the embedding for a long time and that the accuracy of measurement is low.

SUMMARY OF THE INVENTION

It is an object of the present invention to provide an intracorporeal substance measuring assembly which is to be used in an embedded type substance sensor for measuring an intracorporeal substance and which makes it possible to stably measure the analyte for a long time.

It is another object of the present invention to provide a method of producing the intracorporeal substance measuring assembly which is to be used in an embedded type substance sensor for measuring an intracorporeal substance and which makes it possible to measure the analyte stably for a long time.

It is a further object of the present invention to provide an embedded type substance sensor using the intracorporeal substance measuring assembly which makes it possible to measure an analyte stably for a long time.

According to an aspect of the present invention, there is provided an intracorporeal substance measuring assembly provided in an embedded type substance sensor for detecting and measuring an intracorporeal analyte, including:

a detection layer containing at least one fluorescent indicator for generating fluorescence according to the concentration of the analyte; and an optical separation layer being provided on one side of the detection layer, being optically opaque, and permitting the analyte to penetrate therethrough.

According to another aspect of the present invention, there is provided a method of producing an intracorporeal substance measuring assembly provided in an embedded type substance sensor for detecting and measuring an intracorporeal analyte which includes: a detection layer containing at least one fluorescent indicator for generating fluorescence according to the concentration of the analyte; and an optical separation layer being provided on one side of the detection layer, being optically opaque, and permitting the analyte to penetrate therethrough, the method including the steps of:

adding to the detection layer a precursor for forming the optical separation layer, and thereafter binding the precursor to the detection layer.

According to still another aspect of the present invention, there is provided a method of producing an intracorporeal substance measuring assembly provided in an embedded type substance sensor for detecting and measuring an intracorporeal analyte which includes: a detection layer containing at least one fluorescent indicator for generating fluorescence according to the concentration of the analyte; and an optical separation layer being provided on one side of the detection layer, being optically opaque, and permitting the analyte to penetrate therethrough, the method including the step of adhering a peripheral portion of the optical separation layer to the periphery of the detection layer.

According to yet another aspect of the present invention, there is provided an embedded type substance sensor including:

an intracorporeal substance measuring assembly provided in an embedded type substance sensor for detecting and measuring an intracorporeal analyte which including: a detection layer containing at least one fluorescent indicator for generating fluorescence according to the concentration of the analyte; and an optical separation layer being provided on one side of the detection layer, being optically opaque, and permitting the analyte to penetrate therethrough;

a light source for irradiating the detection layer with light from the detection layer side of the intracorporeal substance measuring assembly; and a photo-detector for receiving fluorescence from the detection layer.

According to the intracorporeal substance measuring assembly of the present invention, an optical separation layer being optically opaque and permitting an analyte to penetrate therethrough is provided on one side of a detection layer for generating fluorescence according to the concentration of the analyte, and the detection layer is prevented from making direct contact with the intracorporeal substance, so that it is possible to restrain deterioration of the detection layer, particularly deterioration of a fluorescent indicator in the detection layer, and to obtain stable measurement results even in long-time measurement. In addition, it is possible to prevent light from leaking from the sensor, and to prevent bad effects on the living body tissues around the sensor.

Besides, according to the method of producing an intracorporeal substance measuring assembly of the present invention, it is possible to easily produce the intracorporeal substance measuring assembly having the two-layer structure of the detection layer and the optical separation layer according to the invention.

Further, according to the embedded type substance sensor of the present invention, the intracorporeal substance measuring assembly having the two-layer structure of the detection layer and the optical separation layer of the invention is used, whereby deterioration of the detection layer is restrained, and stable measurement for a long time can be achieved.

The intracorporeal substance measuring assembly according to the present invention is favorably applicable to an embedded type substance sensor for measuring an analyte in a living body, particularly an embedded-in-body type sensor which is adhered to a living body or a part or the whole part of which is embedded in a living body. In addition, the sensor according to the present invention is favorably applicable to continuous or intermittent measurement of an analyte in a living body.

BRIEF DESCRIPTION OF THE DRAWINGS

The above and other objects, features and advantages of the present invention will become apparent from the following description and appended claims, taken in conjunction with the accompanying drawings, in which:

DETAILED DESCRIPTION OF THE PREFERRED EMBODIMENTS

Figure 1:
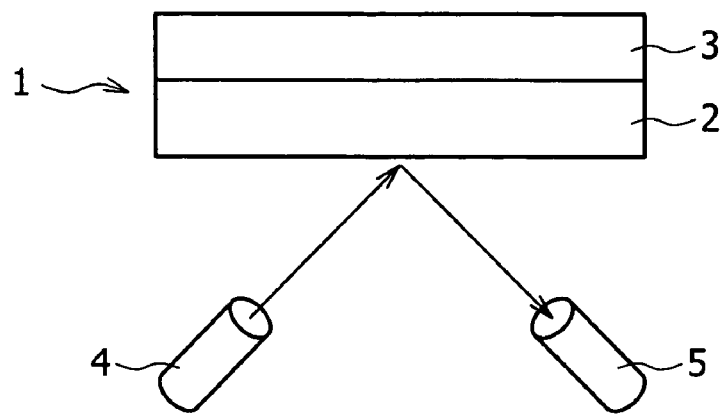
FIG. 1 is an illustration of the principle and configuration of an intracorporeal substance measuring assembly, and a sensor using the same, according to the present invention.

Now, a best mode for carrying out the present invention will be described below referring to the drawings.

Figure 2:
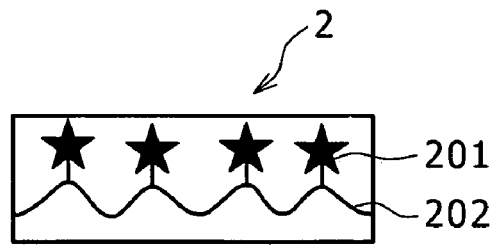
FIG. 2 is a conceptual diagram showing the configuration inside a detection layer in the intracorporeal substance measuring assembly.
Figure 3:
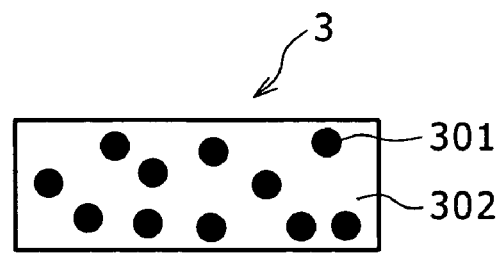
FIG. 3 is a conceptual diagram showing the configuration inside an optical separation layer in the intracorporeal substance measuring assembly.

FIG. 1 is an illustration of the principle and configuration of an intracorporeal substance measuring assembly, and an embedded type substance sensor, according to the present invention, FIG. 2 is a conceptual diagram showing the configuration inside a detection layer in the intracorporeal substance measuring assembly. FIG. 3 is a conceptual diagram showing the configuration inside an optical separation layer in the intracorporeal substance measuring assembly.

The intracorporeal substance measuring assembly is to be used as an indicator layer (hereinafter the intracorporeal substance measuring assembly will be referred to as the indicator layer) in an embedded type substance sensor (hereinafter referred to simply as the sensor).

One embodiment of an indicator layer 1 according to the present invention is, as shown in FIG. 1, composed of a detection layer 2 containing a fluorescent indicator, and an optical separation layer 3 laminated on one side of the detection layer 2. The detection layer 2 and the optical separation layer 3 are chemically coupled to each other.

The detection layer 2, as shown in FIG. 2, has a structure in which a fluorescent indicator 201 is supported by a detection layer base material 202. On the other hand, as shown in FIG. 3, the optical separation layer 3 has a structure in which an opaque substance 301 is supported by an optical layer base material 302.

The indicator layer 1 is so disposed that the optical separation layer 3 is directed to the outside surface side of the sensor, and comes into contact with a living body tissue when provided in the sensor. On the other hand, the detection layer 2 is on the side of the inside of the sensor, and does not make contact with the living body tissue.

In principle, the sensor has a structure in which a light source 4 and a photo-detector 5 are disposed. The light from the light source 4 is radiated onto the detection layer 2, whereby the fluorescent indicator 201 in the detection layer 2 shows fluorescence according to the amount of an analyte, and the fluorescence is received by the photo-detector 5. The photo-detector 5 is a photo-electric conversion device, and outputs an electrical signal according to the amount of light received. From the electrical signal thus outputted, the amount of the analyte is measured. Incidentally, the layout of the light source 4 and the photo-detector 5 may in practice be varied according to the configuration of the sensor.

The fluorescent indicator 201 is selected according to the analyte, and may be any fluorescent indicator inasmuch as its fluorescence property is reversibly varied according to the amount of the analyte. For example, in the case of a sensor for measuring the hydrogen ion concentration or carbon dioxide in a living body, a fluorescent indicator containing a hydroxypyrenetrisulfonic acid derivative as a fluorescent substance may be used; for measurement of saccharide, a fluorescent indicator containing a phenylboronic acid derivative having a fluorescent residual group as a fluorescent substance may be used; and, for measurement of potassium ion, a fluorescent indicator containing a crown ether derivative having a fluorescent residual group as a fluorescent substance may be used.

For measurement of saccharide, those which contain a fluorescent phenylboronic acid derivative as a fluorescent substance may be used; among them, excellent in detection sensitivity is a compound containing two phenylboric moieties and an anthracene moiety as a fluorescent residual group, represented by the following chemical formula (1):

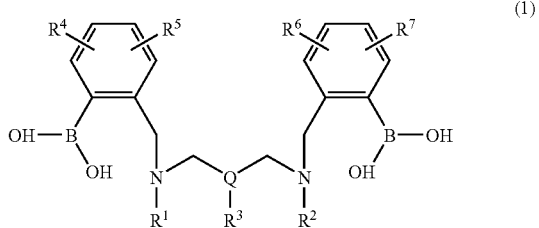

(1)

where Q is a fluorescent residual group, at least one of R1, R2, and R3 is an active group for coupling with the base material of the detection layer. R4, R5, R6, and R7 are each at least one substituent group selected from the group consisting of hydrogen atom, alkyl, alkenyl, allyl, allylalkenyl, substituted alkyl, oxyalkyl, acyl, and halogen atom.

In addition, the fluorescent substituent group in the chemical formula (1) may be substituted. For example, naphthalene, anthracene, phenanthrene, benzanthracene, pyrene, cumarin and the like may be used, among which anthracene is preferred in view of its fluorescence property.

The detection layer 2 is composed of the fluorescent indicator 201 and the detection layer base material 202 for supporting the same. This is for preventing the fluorescent indicator 201 in the sensor from leaking out. The fluorescent indicator 201 and the detection layer base material 202 are preferably forming a covalent bond or forming a bond by an electrical, hydrophobic or other interaction.

Such a detection layer 2 can, for example, be obtained by a method in which the fluorescent indicator 201 having the active group is bonded to the detection layer base material 202 having an active group capable of reacting with the active group of the fluorescent indicator 201.

In this case, a spacer with an appropriate length may be introduced between the two members. Examples of the spacer which can be used include alkyl chains and polyether chains. The introduction of the spacer enhances the kinetic property of the fluorescent indicator 201, thereby enhancing the sensor sensitivity and enhancing the marking efficiency at the time of the introduction reaction.

As the detection layer base material 202 for supporting the fluorescent indicator 201, polymeric substances which are light-transmitting can be used. Among the polymeric substances, particularly preferred are cellulose, polyacrylamide, polyethylene glycol, and polyvinyl alcohol, which are non-limitative examples.

For bonding of the fluorescent indicator 201, it is necessary that an appropriate active group be present in the detection layer base material 202. Where the active group is absent, it is possible to introduce the active group later.

Examples of the two kinds of active groups, namely, both the active group in the fluorescent indicator 201 and the active group in the optical separation layer base material 302, include amino group, carboxylic acid group, hydroxyl group, halo-carboxylic acid group, sulfonic acid group, halo-sulfonic acid group, thiol group, isocyanate group, and isothiocyanate group.

Both the fluorescent indicator 201 having the active group and the detection layer base material 202 having the active group (and, where the spacer is introduced, the spacer also) can be bonded by a reaction in the presence or absence of an appropriate solvent, catalyst, or condensing agent, as required.

Where a fluorescent phenylboronic acid derivative is to be bonded to the detection layer base material 202, the bonding can be achieved, for example, by a method in which the detection layer base material 202 is bonded (R1, R2) from either one or both of the nitrogen atoms in the chemical formula (1), or the detection layer base material 202 is bonded (R3) to the fluorescent residual group, with or without the above-mentioned appropriate spacer between the fluorescent indicator 201 and the detection layer base material 202.

The optical separation layer 3 is composed of the opaque substance 301 and the optical separation layer base material 302 for supporting the same. The optical separation layer 3 has the functions to shield the excitation light coming from the light source 4, to shield the fluorescence generated from the fluorescent indicator 201 in the detection layer 2, to shield external light other than the fluorescence generated from the fluorescent indicator 201, and to exclude the influences of colored substances and fluorescent substances present in the living body.

These shielding functions not only enhances the reliability of measurements but also has the effect of preventing bad influences of the excitation light and the fluorescence on the living body tissues around the sensor, which effect is required of the sensor.

It suffices for the opaque substance 301 used in the optical separation layer 3 to prevent the excitation light coming from the light source 4 and the fluorescence generated by the fluorescent indicator 201 from penetrating therethrough; therefore, as the opaque substance 301, there may be used those substances which do not permit UV rays, visible rays, IR rays and the like rays to penetrate therethrough and which do not reflect the rays. Particularly where UV rays are used as the excitation light, this is important for ensuring that the UV rays are not radiated to the exterior of the sensor.

Examples of the opaque substance 301 which can be used include carbon black, fullerene, and carbon nanotube. The opaque substance 301 can be supported on the optical separation layer base material 302 by formation of covalent bond, electric or a hydrophobic interaction. In addition, the opaque substance 301 can be supported also by enclosing it in a polymeric structure of the optical separation base material 302.

As the optical separation base material 302, there can be used polymeric substances, which may be cross-linked or modified.

Examples of the polymeric substances which can be used include dextran, polyacrylamide, polyethylene glycol, polyvinyl alcohol, and polyamide.

In addition, as the optical separation layer base material 302, a polymeric porous film formed by a phase transition method can be used. The phase transition method for obtaining the polymeric porous film for the optical separation layer base material 302 in the present invention is a method which has conventionally been generally well known, and, for example, a wet type film forming method may be used. The wet type film forming method is a technique sufficiently established by Loeb and Sourirajan (refer to Adv. Chem. Ser. 38, 117, 1963), and is described in detail in, for example, "Synthetic Polymer Membranes, a Structural Prespective", Ed. 2 (R. R Kesting, J. Wiley and Sons). This method is a method in which a polymeric compound is dissolved in a solvent to prepare a film forming raw liquid, and then the film forming raw liquid formed into a desired shape is immersed in a nonsolvent for the polymeric compound, to obtain a microporous film. Materials which can be used for forming the polymeric porous film include cellulose derivatives, polysulfone-based resins, polyamide-based resins, and aromatic polyether-ketone resins. Examples of the cellulose derivatives include cellulose acetate, and cellulose nitrate. Examples of the polysulfone-based resins include polysulfones, polyether sulfones, and polysulone sulfates. Examples of the aromatic polyether-ketone based resins include polyether-ether-ketones, and polyallylether-ketones. The thickness in dried state of the polymeric porous film in the present invention is preferably 5 to 100 µm, more preferably 5 to 50 µm, and further preferably 10 to 20 µm. Where the thickness is smaller than the lower limit, problems of insufficient light-shielding property or insufficient strength will be generated; on the other hand, where the thickness is greater than the upper limit, response speed is lowered.

In addition, the average pore diameter of the polymeric porous film in the present invention is preferably 0.001 to 0.1 µm, more preferably 0.005 to 0.01 µm. These values are measured by shooting the surface of the polymeric porous film on an electron microscope, and are the smaller values of the values on the outside and the values on the inside. Besides, where it is desired to accelerate the response speed even while sacrificing the time variation of response property, the average pore diameter is further preferably 0.01 to 0.05 µm.

In addition, it is preferable that the value of (glucose)/(bovine serum albumin) of the initial permeability velocity ((number of permeated molecules)/(film unit area)·(unit time)) of the polymeric porous film in the present invention is in the range of from 10 to infinity, more preferably from 20 to infinity, and further preferably from 40 to infinity. The initial permeability velocity was calculated from the experimental results obtained by use of a diffusion cell which is ordinarily used for evaluation of dialyzers. The experimental conditions were a unit chamber volume of 50 mL, an effective surface area of the test film of 4.9 $cm^2$, and a temperature of 37° C. A phosphoric acid buffer physiological saline solution containing 100 mg/mL (w/v) of glucose and 5% (w/v) of bovine serum albumin was placed as a pseudo-humor liquid in a supply-side cell, whereas only the phosphoric acid buffer physiological saline solution was placed in a receiving-side cell, and variations in the concentrations of the components in the cells were measured periodically.

Where dextran, for example, is used for the optical separation layer base material 302, the opaque substance 301 is dispersed in a dextran solution, and cross-linking is effected, whereby the opaque substance 301 can be supported on the network structure of dextran.

In addition, the optical separation layer 3 has the function to permit the analyte to penetrate therethrough and the function to prevent the penetration therethrough of at least one living body component other than the analyte. This is achieved by controlling the molecular weight, cross-linking degree, and chemical structure of the optical separation layer base material 302, and thereby forming appropriate-sized gaps in the optical separation layer 3. Other than this, a method of forming pores by physical or chemical means and the like may also adopted.

Some living body components obstruct the interaction between the fluorescent indicator 201 and the analyte as well as fluorescence emission characteristics. Therefore, it is very useful to provide the optical separation layer 3 in the indicator layer 1 with the function of preventing these living body components from reaching the detection layer 2.

For example, an optical separation layer 3 capable of excluding blood cells, living body-derived proteins and polysaccharides and the like is preferable. In the case of a sensor for dealing with saccharides or ions as the analyte, it is possible to form an optical separation layer which permit only the analyte to penetrate therethrough and which prevents passage therethrough of blood cells and proteins, by utilizing the difference in molecular weight.

As the optical separation layer base material 302, a polymeric substance with excellent biocompatibility is preferably used, for ensuring that the optical separation layer 3 itself constituting the outermost surface of the indicator layer 1 is not varied in physical properties due to various bio-reactions at the surface and that the influence of the indicator layer 1 on the living body is reduced, when the sensor is embedded in the living body.

Examples of such polymeric substance include dextran, cellulose derivatives, polyacrylamide, polyethylene glycol, polyvinyl alcohol, cellulose, polyfulfone-based resins, polyamide-based resins, and aromatic polyether-ketone resins. In addition, for enhancing the biocompatibility, the surface of the polymeric substance may be modified or a compound may be bonded to the surface.

Further, the optical separation layer 3 has the function to prevent passage therethrough of living body substances which may deteriorate the detection layer 2 or may deviate fluorescence characteristics. Specifically, radicals, oxidizing substances, and reducing substances which are present in a living body and may deteriorate the fluorescent indicator 201, substances which accelerate photolysis of the fluorescent indicator 201 and the like are inactivated or adsorbed, to thereby prevent these substances from reaching the detection layer 2. This is based on the fact that, when living body substances which influences the interaction between the fluorescent indicator 201 and the analyte reach the detection layer, the fluorescence characteristics of the fluorescent indicator 201 are changed, or the fluorescence or colored living body substances themselves reach the detection layer 2, resulting in deviations (errors) in the results of measurements. In view of this, these substances are prevented from reaching the detection layer 2.

For this purpose, a substance having these actions is added to the optical separation layer base material 302, or an opaque substance 301 which itself has these actions is used.

Specifically, this is enabled by a method in which vitamin E, polyphenols, metal chelates or the like are modifyingly added to or supported on the optical separation layer base material 302. Besides, such a function can be obtained by using carbon black, fullerene or a derivative thereof as one of the opaque substances 301. Further, an anti-oxidizing agent or radical activating substance may be modifyingly imparted to the optical separation layer base material 302, or activated carbon having the action of adsorbing obstructing substances may be used as one of the opaque substances 301.

The provision of the optical separation layer 3 with the function of inactivating or adsorbing the living body components having influences on the detection of an analyte is useful for obtaining accurate, reproducible measurement results.

By providing the optical separation layer 3 with these functions, it is possible to protect the detection layer 2 and to maintain the analyte detecting and measuring function for a long time.

In addition, it is ideal for the optical separation layer 3 to selectively permit only the analyte to penetrate through the optical separation layer 3 to the detection layer and to prevent the other living body substances from penetrating through the optical separation layer 3 to the detection layer. In practice, however, it is very difficult, or impossible depending on the analyte, to selectively permit only the analyte to pass through the optical separation layer 3. In view of this, in the optical separation layer 3 in this embodiment, at least one of the living body substances which hamper the fluorescence of the detection layer 2 or deteriorate the detection layer 2 is prevented from penetrating through the optical separation layer 3, whereby it is possible to enhance the accurateness of measurement and to obtain stability of measurement for a long time.

The optical separation layer 3 and the detection layer 2 are chemically bonded to each other. The chemical bond means covalent bond, ionic bond, hydrophobic bond and the like.

The bonding between the optical separation layer 3 and the detection layer 2 is achieved, for example, by bonding them through a cross-linking agent which has at both ends thereof active groups for bonding between the active group present in the optical separation layer 3 and the active group present in the detection layer 2.

In addition, the optical separation layer base material 302 of the optical separation layer 3 can be chemically bonded to the detection layer 2 simultaneously with the cross-linking of the optical separation layer base material 302.

For example, the chemical bond can be formed by a method wherein the optical separation layer base material 302 or its precursor containing the opaque substance 301 and a cross-linking agent are laminated on the detection layer 2 and brought into reaction with the detection layer 2, after forming the detection layer 2 first.

For example, where dextran is used for the optical separation layer base material 302, holding of the opaque substance 301 and bonding to the detection layer 2 can be simultaneously performed by adding a dextran solution with the opaque substance 301 dispersed therein to the detection layer 2 and thereafter effecting the cross-linking.

Besides, where a polymeric porous film is used as the optical separation layer base material 302, a peripheral portion of the optical separation layer base material 302 can be adhered to the periphery of the detection layer by use of a resin adhesive (epoxy-based one, silicone-based one, etc.). In addition, the bond between the detection layer 2 and the optical separation layer 3 can also be formed by a method in which a polymerizable compound having an active group to be bonded to the active group present in the detection layer 2 is used, and the polymerizable compound is polymerized in the porous structure of the polymeric porous film. Examples of the polymerizable compound having the active group include ethylene glycol-diglycidyl ether, alkyl dihalides, glycidyl methacrylate, N,N'-methylenebisacrylamide, N,N'-(1, 2-dihydroxyethylene)-bisacrylamide, ethylene glycol dimethacrylate, and ethylene dimethacrylate.

Now, an embedded-type substance sensor using the indicator layer as above will be described below.

In principle, it suffices for the sensor to have a light source 4 for emitting excitation light, and a photo-detector 5 for receiving fluorescence; in practice, however, an amplifier for amplifying an output signal from the photo-detector 5, a microprocessor for processing the amplified signal, a transmitter for transmitting the data to the exterior, a battery and the like are further needed. Since the sensor itself is to be entirely embedded in a living body, these component parts must all be incorporated in a single package.

In the case of a perfectly embedded type sensor, the light source 4 for emitting light with at least one wavelength, and the photo-detector 5 (photo-electric conversion device) capable of detecting the light with at least one wavelength are incorporated as a fluorescence detection system in a package capable of maintaining liquid-tightness.

The indicator layer 1 constituting the intracorporeal substance measuring assembly according to the present invention is provided in a part of the package. In this instance, the light source 4 and the photo-detector 5 are so laid out that the side of the optical separation layer 3 is disposed to the outside for making contact with a living body, that the excitation light from the light source 4 is radiated onto the side of the internally provided detection layer 2, and that the fluorescence from the detection layer 2 can be received by the photo-detector 5.

As the light source 4, there can be used, for example, a light emitting diode or a semiconductor laser. The excitation light from the light source 4 is radiated onto the detection layer 2 by way of an optical fiber, a lens or lenses, a mirror, a prism, an optical filter and the like, as required. On the other hand, the photo-detector 5 is a photo-electric conversion device, and, for example, a photo-diode, a photo-transistor or the like are used as the photo-detector 5.

Then, the analog electrical signal from the photo-detector 5 is amplified and converted into a digital signal, to be transmitted to the exterior, by an amplifier, a micro-processor, and a transmitter. In order to transmit the signal to the exterior, for example, an antenna may be provided in the inside of the sensor or in an external portion kept liquid-tight. Or, alternatively, the signal may be transmitted by percutaneously passing it in a living body.

A more specific example of the perfectly embedded type sensor will be described.

Figure 4:
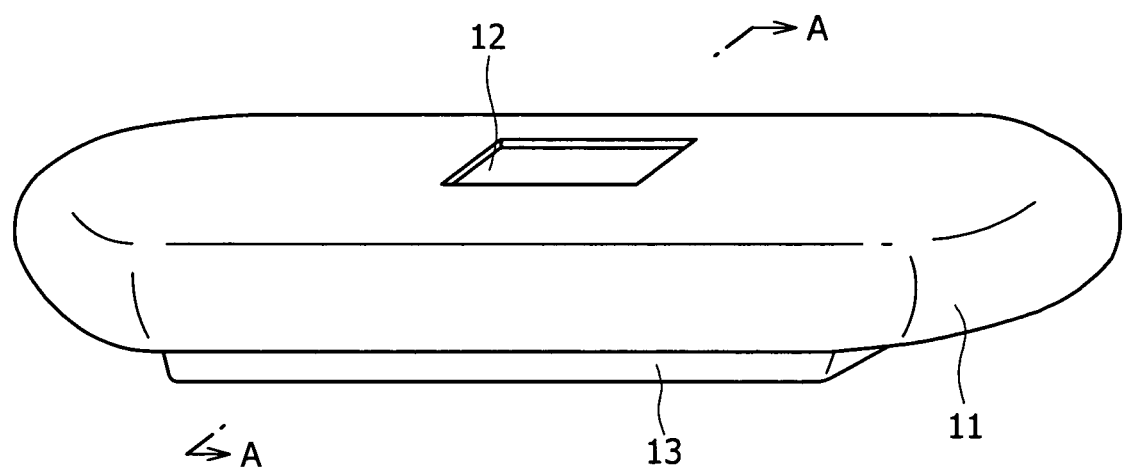
FIG. 4 is a perspective view showing the appearance of a perfectly embedded type sensor.
Figure 5:
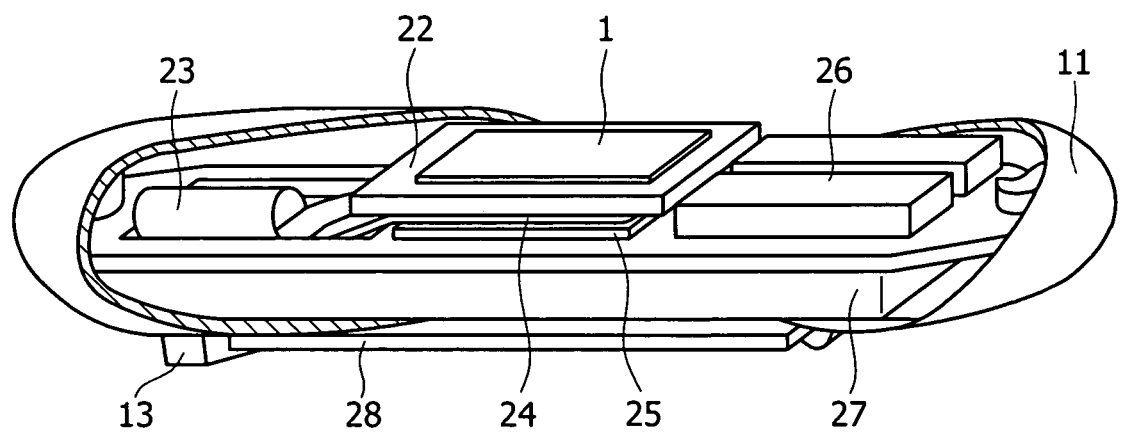
FIG. 5 is a partly broken perspective view showing the inside structure of the perfectly embedded type sensor.
Figure 6:
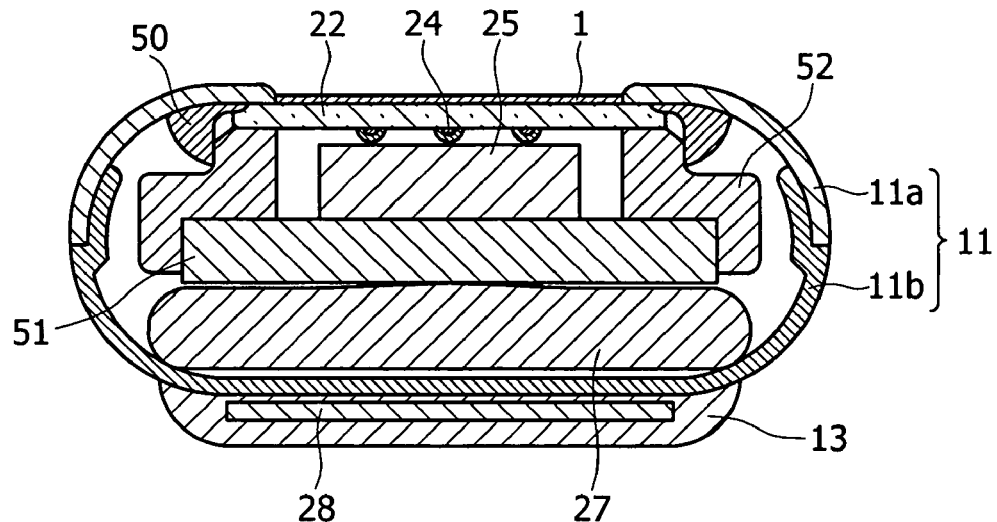
FIG. 6 is a sectional view along A-A of FIG. 4.
Figure 7:
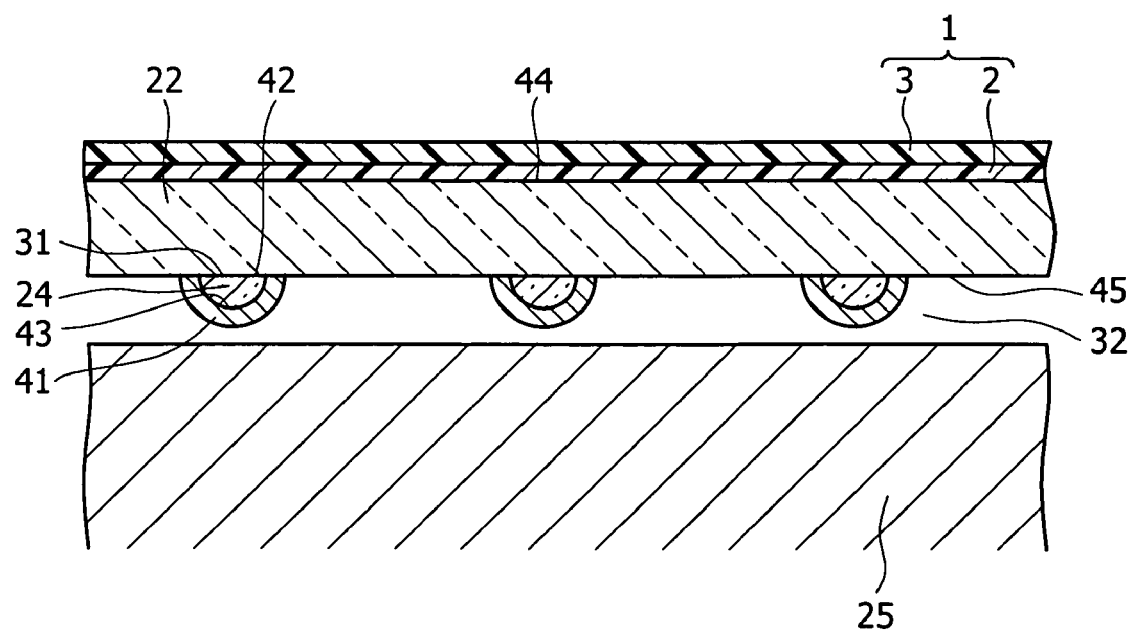
FIG. 7 is an enlarged sectional view of such portions as an indicator layer, an optical waveguide, and a photo-detector in the section shown in FIG. 6.

FIG. 4 is a perspective view showing the apperance of a perfectly embedded type sensor, FIG. 5 is a partly broken perspective view showing the inside structure of the detection device, FIG. 6 is a sectional view along line A-A of FIG. 4, and FIG. 7 is an enlarged sectional view of an indicator layer, an optical waveguide, a photo-detector and the like in the section shown in FIG. 6.

On appearance, the sensor has a housing 11 for packing the sensor's inside so as to maintain liquid-tightness, a window portion 12 for exposing only the indicator layer 1, and an antenna portion 13 for transmission between the exterior of the living body and the system.

The sensor's inside incorporates the indicator layer 1 for sensing the concentration of an analyte, a transparent layer 22 provided so as to shut the window portion 12 for maintaining the inside in a liquid-tight condition and kept in close contact with the indicator layer 1, a light source 23 for emitting excitation light, an optical waveguide 24 for guiding the light from the light source 23 to the indicator layer 1, a photo-detector 25 for detecting the fluorescence from the indicator layer 1, an integrated circuit 26 for processing signal data fed from the photo-detector 25, and a battery 27 as an internal power source.

The indicator layer 1 is disposed on the outside of and in close contact with the transparent layer 22 which is impervious to liquids. The transparent layer 22, together with the housing 11, keep the sensor's inside liquid-tight from the exterior. The housing 11 is preferably formed of a blank material excellent in biocompatibility, such as titanium.

In this sensor, the light from the light source 23 is guided through the optical waveguide 24 constituting a light emission portion, and is radiated as excitation light onto the indicator layer 1, whereby the indicator layer 1 shows fluorescence according to the concentration of an analyte in a living body, and the fluorescence is converted into an electrical signal by the photo-detector 25.

The optical waveguide 24 is so disposed as to be sandwiched between the indicator layer 1 and the photo-detector 25. The optical waveguide 24 is, for example, an optical fiber or the like.

The optical waveguide 24 is provided with a light-shielding layer 42 recessed to the side of the photo-detector 25. As shown in the figure, the light-shielding layer 41 is made, for example, by working a metal pipe such as a stainless steel pipe so as to cover the photo-detector 25 side of the optical waveguide 24, or by plating only the photo-detector 25 side of the optical waveguide 24. Incidentally, the inside surface 43 (namely, the optical waveguide 24 side) of the light-shielding layer 41 is preferably light-reflecting.

The light guided from the light source 23 by the optical waveguide 24 as above is not radiated to the photo-detector 25 side, due to the presence of the light-shielding layer 41, but is radiated only to the indicator layer 1.

The photo-detector 25 is a light receiving device for receiving fluorescence from the indicator layer 1 and converting the fluorescence into an electrical signal according to the amount of light received.

An appropriate gap 32 is provided between the transparent layer 22 and the photo-detector 25. The portion of the gap 32 is preliminarily filled with a gas having a refractive index of about 1 (one), such as air and nitrogen gas.

The detection layer 2 in the indicator layer 1 receives the excitation light, exhibits fluorescence according to the concentration of an analyte, and radiates the fluorescence as diffused light to the surroundings. The fluorescence thus radiated passes through the transparent layer 22, passes through the gap 32, and is radiated onto the photo-detector 25, to be converted into an electrical signal. In this instance, the light radiated from the optical waveguide 24 is radiated onto only the indicator layer 1 in the opposite direction relative to the photo-detector 25, with the result that the excitation light is not radiated directly onto the photo-detector 25.

On the other hand, the photo-detector 25 side surface of the transparent layer 22 is in contact with the gas having a refractive index of about 1 (one), such as air and nitrogen gas. Therefore, the total reflection angle of the excitation light on the interface 44 between the transparent layer 22 and the indicator layer 1 must necessarily be greater than the total reflection angle on the interface 45 of the transparent layer 22 on the opposite side. As a result, the excitation light totally reflected on the interface 44 is substantially prevented from being radiated onto the photo-detector 25, and the photo-detector 25 can efficiently receive the fluorescent component from the indicator layer 1, of the light components with which it is irradiated.

An integrated circuit 26 has a structure in which an amplifier, a micro-processor, and a transmitter are integrated with each other. The integrate circuit 26 processes the electrical signal fed from the photo-detector 25, temporarily stores the processed signal, and, at appropriate time, transmits the signal to an extracorporeal system via the antenna portion 13 disposed on the outside surface of the housing.

The antenna portion 13 has an antenna coil 28 incorporated therein in the state of being enclosed in a resin or the like so as not to make contact with humor.

Incidentally, in the inside of the housing 11, the transparent layer 22 is attached to the periphery of the window portion 12 of the housing 11 by an adhesive 50, the integrated circuit 26 and the detector 25 are disposed on a spacer substrate 51, and the spacer substrate 51 is supported by a spacer 52, whereby a predetermined gap 32 is maintained between the detector 25 and the transparent layer 22. With the predetermined gap 32 thus maintained between the detector 25 and the transparent layer 22 by the spacer substrate 51 and the spacer 52, the predetermined gap 32 can always be maintained even in the case where a soft package made of a resin instead of a metal is used as a member constituting the housing 11.

EXAMPLE

Now, the present invention will be described further below by way of Examples.

Example 1

Preparation of Indicator Layer for Measuring Glucose, 1

(1) Synthesis of Fluorescent Indicator [9,10-bis((N-methyl-N-(ortho-boronobenzyl)amino)methyl)anthracene-2-carboxylic acid]

A. Synthesis of Methyl-9,10-bis(bromomethyl)anthracene-2-carboxylic acid 360 mL of methyl-9,10-dimethylanthracene-2-carboxylic acid, 540 mg of N-bromosuccinimide, and 5 mg of benzoyl peroxide were added to a mixture of 4 mL of chloroform and 10 mL of carbon tetrachloride, followed by heating at reflux for 2 hr. After removal of solvent, the residue was extracted with methanol, to obtain 430 mg of methyl-9,10-bis(bromomethyl)anthracene-2-carboxylic acid.

B. Synthesis of Methyl-9,10-bis(aminomethyl)anthracene-2-carboxylic acid 400 mg of methyl-9,10-bis(bromomethyl)anthracene-2-carboxylic acid obtained in A above was dissolved in 60 mL of chloroform, then 8 mL of 2 M methylamine solution in methanol was added thereto, followed by stirring at room temperature for 4 hr. After removal of solvent, purification was conducted on a silica gel column using methanol/chloroform as an eluent, to obtain 235 mg of methyl-9,10-bis(aminomethyl)anthracene-2-carboxylic acid.

C. Synthesis of 9,10-Bis((N-methyl-N-(ortho-boronobenzyl)amino)methyl)anthracene-2-carboxylic acid 200 mg of methyl-9,10-bis(aminomethyl)anthracene-2-carboxylic acid obtained in B above, 700 mg of 2-(2-bromomethylphenyl)-1,3-dioxaborinane, and 0.35 mL of N,N-diisopropylethylamine were dissolved in 3 mL of dimethylformamide, followed by stirring at room temperature for 16 hr. After removal of solvent, purification was conducted on a silica gel column using methanol/chloroform as an eluent, to obtain 194 mg of a methyl ester.

The methyl ester was dissolved in 5 mL of methanol, and 1 mL of 4 N sodium hydroxide was added thereto, followed by stirring at room temperature for 10 hr. Thereafter, the reaction mixture was neutrailized with hydrochloric acid, inorganic salts were removed by gel filtration, to obtain 180 g of 9,10-bis((N-methyl-N-(ortho-boronobenzyl)amino)methyl)anthracene-2-carboxylic acid.

The thus obtained 9,10-bis((N-methyl-N-(ortho-boronobenzyl)amino)methyl)anthracene-2-carboxylic acid had a melting point of 121° C., and $^1$H-NMR data in DMSO-$d_6$ of 2.15 ppm (d, 6H, N—CH$_3$), 4.10 ppm (m, 4H, N—CH$_2$-benzene), 4.45 ppm of (m, 4H, N—CH$_2$-anthracene), and 7.55 to 8.90 ppm (m, 15H, N—CH$_2$-aromatic).

Chemical formulas for representing the process of preparation of the above fluorescent indicator is shown below.

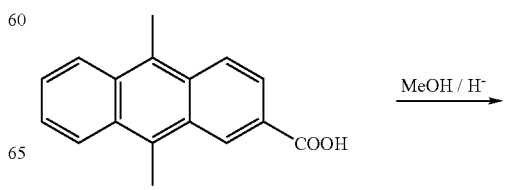

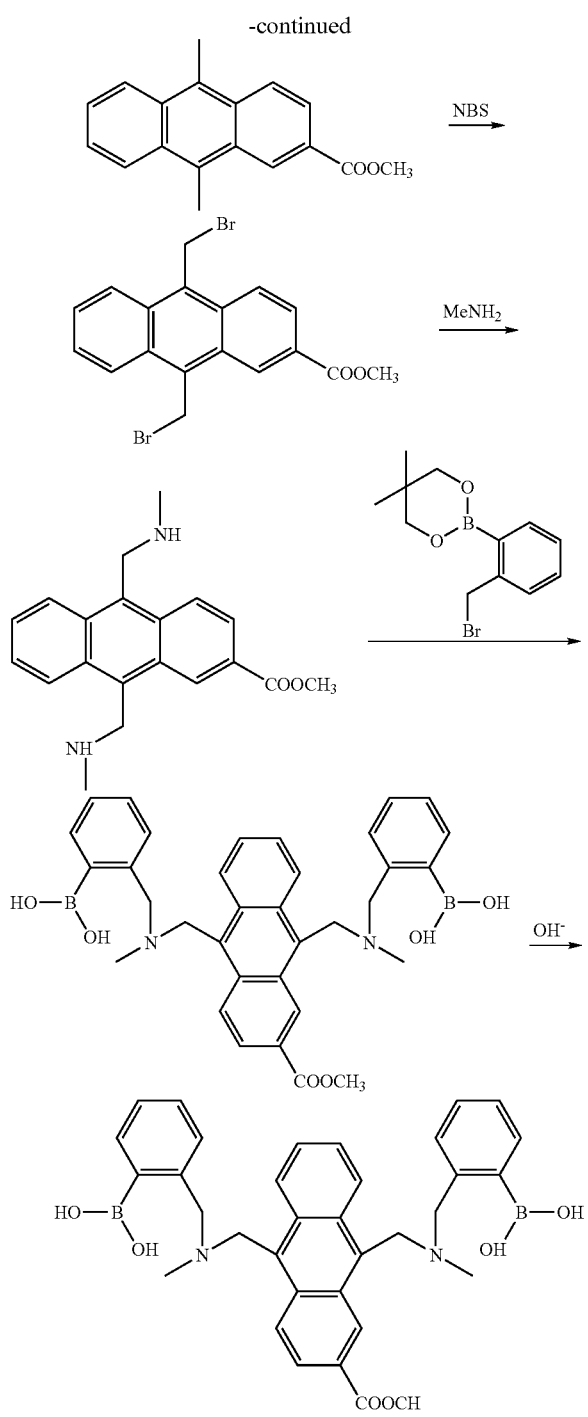

(2) Preparation of Detection Layer for Measuring Glucose 1.25 g of ethylene glycol diglycidyl ether was dissolved in 4 mL of dimethyl sulfoxide, then 16 mL of distilled water containing 60 mg of sodium hydroxide was added to the solution, and the resulting mixture was placed in a 10 cm×10 cm shallow rectangular stainless steel vessel.

A reproduced cellulose film (Cuprophan) cut to 10 cm square was calmly immersed in the mixture in the vessel, reaction was allowed at room temperature for 20 min, and the film was calmly washed with 40 mL of distilled water four times.

Subsequently, the film was immersed in 20 mL of a 4.2% (w/v) aqueous solution of 1,6-hexadiamine contained in a similar vessel, reaction was allowed at room temperature for 2 hr, then the reaction mixture was removed, the film was washed with 40 mL of distilled water four times, and the film was calmly washed with 20 mL of dimethylformamide two times, to obtain an activated cellulose film.

20 mg of 9,10-bis((N-methyl-N-(ortho-boronobenzyl) amino)methyl)anthracene-2-carboxylic acid obtained in (1) above, 12 mg of 1-(3-(dimethylamino)propyl)-3-ethylcarbodiimide, and 8 mg of 1-hydroxybenzotriazole were dissolved in 10 mL of dimethylformamide, the solution was placed in a similar vessel, and the activated cellulose film obtained by the above reaction was placed in the solution in the vessel.

Reaction was allowed at room temperature for 17 hr, then the film was washed with 20 mL of dimethylformamide three times, was washed with 40 mL of 0.01 N hydrochloric acid two times, was washed with 40 mL of distilled water three times, and was washed by immersing the film in 50 mM phosphoric acid buffer (pH=7.0) for not less than 10 hr.

(3) Preparation of Indicator Layer 7 g of dextran was dissolved in 175 mL of distilled water under stirring at 50° C., 5 g of carbon black was added to the solution, and the mixture was subjected to ultrasonic treatment until carbon black was dispersed uniformly. Then, 3.5 mL of 50% aqueous solution of sodium hydroxide and 6.5 g of ethylene glycol diglycidyl ether were added to the mixture, and the resulting mixture was stirred at 45° C. for 30 min. The solution thus obtained was used as a precursor for forming an optical separation layer. At this stage, cross-linking and polymerization of dextran and introduction of functional groups to the polymer occur partly.

Further, 230 mL of distilled water was added to the solution, followed by stirring, and the mixed solution was placed in a sprayer.

The glucose measuring detection layer prepared in (2) above was fixed to a flat glass plate, and the above mixed solution was uniformly sprayed onto the detection layer, followed by drying in a 45° C. oven for 30 min, to form an optical separation layer. By the drying under heating, the cross-linking and polymerization in the inside of dextran is made to proceed further to form a network structure, and binding to the detection layer is performed. In this way, a thin film for constituting the indicator layer according to the present invention was obtained.

Example 2

Preparation of Indicator Layer for Measuring Glucose, 2

A. Preparation of Detection Layer 8 g of aqueous perchloric acid solution (effective chlorine concentration: 5%) and 5 mL of 12 N aqueous sodium hydroxide solution were mixed with 15 mL of distilled water, and the mixed solution was placed in a 10 cm×10 cm shallow rectangular stainless steel vessel, followed by cooling to 0° C. A polyacrylamide film cut to 10 cm square was calmly immersed in the mixed solution in the vessel, and reaction was allowed at −5° C. for 2 hr.

The reaction liquid was removed, the film was calmly washed with 40 mL of distilled water four times and with 20 mL of dimethylformamide two times, to obtain an activated polyacrylamide film.

20 mg of 9,10-bis((N-methyl-N-(ortho-boronobenzyl) amino)methyl)anthracene-2-carboxylic acid synthesized in Example 1, 12 mg of 1-(3-(dimethylamino)propyl)-3-ethyl-carbodiimide, and 8 mg of 1-hydroxybenzotriazole were dissolved in 10 mL of dimethylformamide, the solution was placed in a similar vessel, and the activated polyacrylamide film prepared by the above reaction was immersed in the solution in the vessel.

Reaction was allowed at room temperature for 17 hr, then the film was washed with 20 mL of dimethylformamide three times, with 40 mL of 0.01 N hydrochloric acid two times, and with 40 mL of distilled water three times, and the thus washed film was washed by immersing the film in 50 mM phorphoric acid buffer (pH=7.0) for not less than 10 hr.

B. Imparting Optical Separation Layer to Detection Layer 7 g of dextran was dissolved in 175 mL of distilled water under stirring at 50° C., then 5 g of carbon black was added to the solution, and the mixture was subjected to ultrasonic treatment until carbon black was dispersed uniformly. Then, 3.5 mL of 50% aqueous sodium hydroxide solution and 6.5 g of ethylene glycol diglycidyl ether were added to the mixture, followed by stirring at 45° C. for 30 min, to obtain a precursor for forming an optical separation layer. Further, the solution was added to 230 mL of distilled water, and the mixed solution was placed in a sprayer.

The detection layer prepared in A above was fixed to a flat glass plate, the above mixed solution was uniformly sprayed onto the detection layer, followed by drying in a 45° C. oven for 30 min to form the optical separation layer, whereby a thin film for constituting an indicator layer according to the present invention was obtained.

Example 3

Preparation of Indicator Layer for Measuring Glucose, 3

7 g of detran was dissolved in 175 mL of distilled water under stirring at 50° C., then 5 g of fullerene was added to the solution, and the mixture was subjected to ultrasonic treatment until fullerene was dispersed uniformly. Then, 3.5 mL of 50% aqueous sodium hydroxide solution and 6.5 g of ethylene glycol diglycidyl ether were added to the mixture, followed by stirring at 45° C. for 30 min, to obtain a precursor for forming an optical separation layer. Further, the solution was added to 230 mL of distilled water, and the mixed solution was placed in a sprayer.

The glucose measuring detection layer prepared in (2) of Example 1 above was fixed to a flat glass plate, and the above mixed solution was uniformly sprayed onto the detection layer, followed by drying in a 45° C. oven for 30 min to form the optical separation layer, whereby a thin film to be an indicator layer according to the present invention was obtained.

Example 4

Preparation of Indicator Layer for Measuring Glucose, 4

20 g of cellulose diacetate was dissolved in 150 g of dimethylformamide, 50 g of triethylene glycol was added to the solution, 6 g of carbon black was further added to the solution, and the resulting mixture was dispersed under stirring until the mixture became uniform. The slurry thus obtained was cast on a flat glass plate by use of an applicator with a clearance adjusted to 50 μm, the cast material was solidified in an aqueous 30% solution of DMF, then the assembly was immersed in an aqueous 5% solution of glycerin, the film peeled from the flat glass plate was recovered, the film was sufficiently washed in an aqueous 5% solution of glycerin, and was then dried at room temperature for not less than 24 hr, to obtain an optical separation film. The average pore diameter in the film surface as observed on an electron microscope was 0.01 μm, and the (glucose permeability velocity)/(bovine serum albumin permeability velocity) was 71.6.

The glucose measuring detection layer prepared in (2) of Example 1 above was fixed to a flat glass plate, the optical separation layer blanked in a larger size from the detection layer was laminated on the detection layer, and the periphery of the laminate was fixed with a resin adhesive, to obtain a thin film to be an indicator layer according to the present invention.

Evaluation 1

Evaluation of Glucose Response Property of Indicator Layer

The glucose response property of the indicator layer was evaluated. Incidentally, for comparison, an indicator layer using only the glucose measuring detection layer prepared in (2) of Example 1 (i.e., an indicator layer without an optical separation layer) was used as a Comparative Example (here and hereinafter).

To perform evaluation, the indicator layer was fixed to an evaluation apparatus, and the response of fluorescence intensity to glucose concentration was evaluated in blood plasma.

Figure 8:
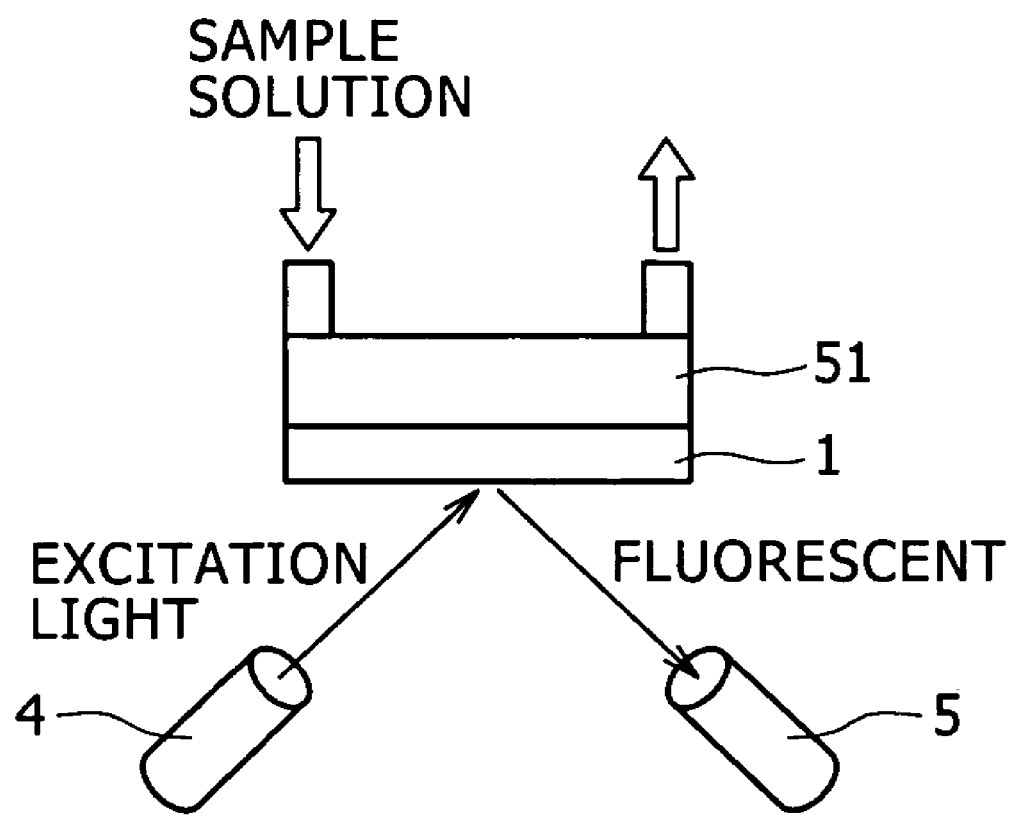
FIG. 8 is a schematic diagram showing the structure of an evaluation apparatus for evaluating the glucose response property of the indicator layer.

FIG. 8 is a schematic diagram showing the structure of an evaluation apparatus for evaluating the glucose response property of an indicator layer.

The evaluation apparatus comprises a flow cell 51 to which the indicator layer 1 is fixed and in which a liquid can be circulated, a light source 4 for irradiating the surface, to which the indicator layer 1 is fixed, of the flow cell 51 with excitation light, and a photo-detector 5 for receiving the fluorescence (fluorescent light) radiated from the indicator 1. Incidentally, in the actual apparatus, the excitation light from the light source 4 is the light which is guided by an optical fiber from a light emitting diode or the like serving as the light source and which is radiated toward the indicator layer. In addition, the photo-detector 5 is so structured that the fluorescence from the indicator layer is received by an optical fiber and guided to a fluorescence spectrophotometer. Here, an excitation wavelength of 380 nm and a measurement wavelength of 440 nm were used.

Figure 9:
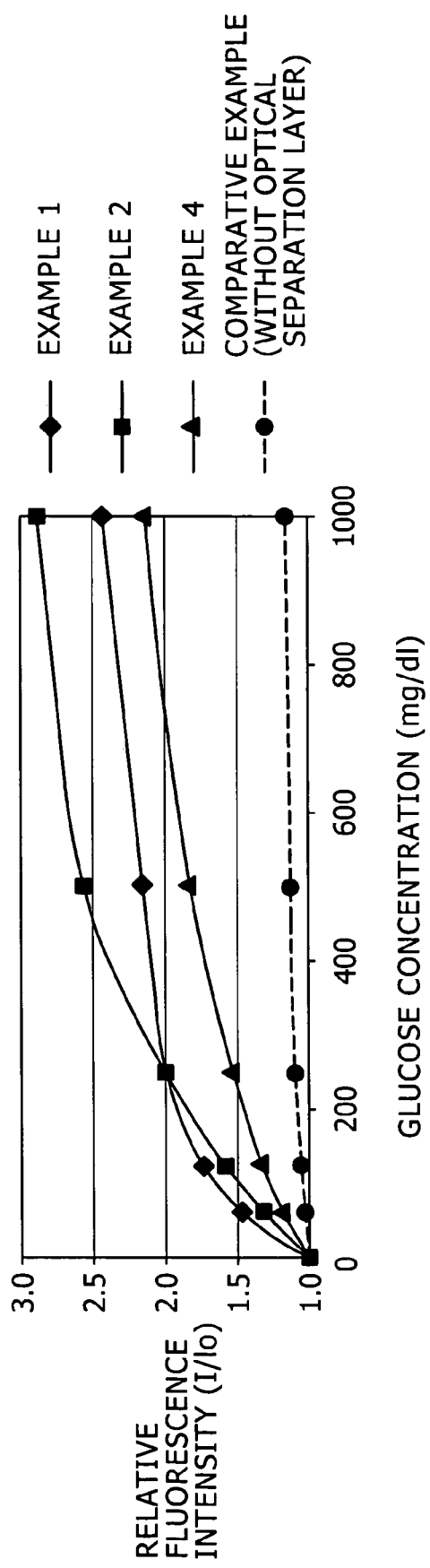
FIG. 9 is a graph showing the results of evaluation of the glucose response property of the indicator layer.

FIG. 9 is a graph showing the results of evaluation of the glucose response property of the indicator layers prepared in Examples 1 and 2 and Comparative Example.

Both the indicator layers prepared respectively in Example 1 in which the detection layer base material in the detection layer was cellulose and Example 2 in which the detection layer base material in the detection layer was polyacrylamide gave good glucose response properties, but, on the other hand, the indicator layer prepared in Comparative Example lacking the optical separation layer gave little response.

This is considered to be due to the following. In Comparative Example, due to the lacking of the optical separation layer, the substances in the blood plasma obstructed the interaction with the fluorescent indicator, and the fluorescence generated could not be collected efficiently. Or, alternatively, due to the lacking of the optical separation layer, light coming from other substances than the fluorescent indicator was picked up.

Thus, it is seen that in Examples 1 and 2 according to the present invention, the optical separation layer is used, whereby glucose can be measured assuredly.

Evaluation 2

Evaluation of Excitation Light and Fluorescence Shielding Effect of Indicator Layer The indicator layer was fixed to the above-mentioned evaluation apparatus, the indicator layer was irradiated with 405 nm excitation light, and leakage of excitation light and fluorescence was measured by a photo-detector disposed on the optical separation layer side on the upper side of the sensor. As the photo-detector, a photo-detector capable of continuously sensing the rays in the range from 360 nm to 500 nm was used.

Comparative evaluation was conducted by use of the indicator layers prepared in Examples 1 and 2 and the indicator layer of Comparative Example.

Figure 10:
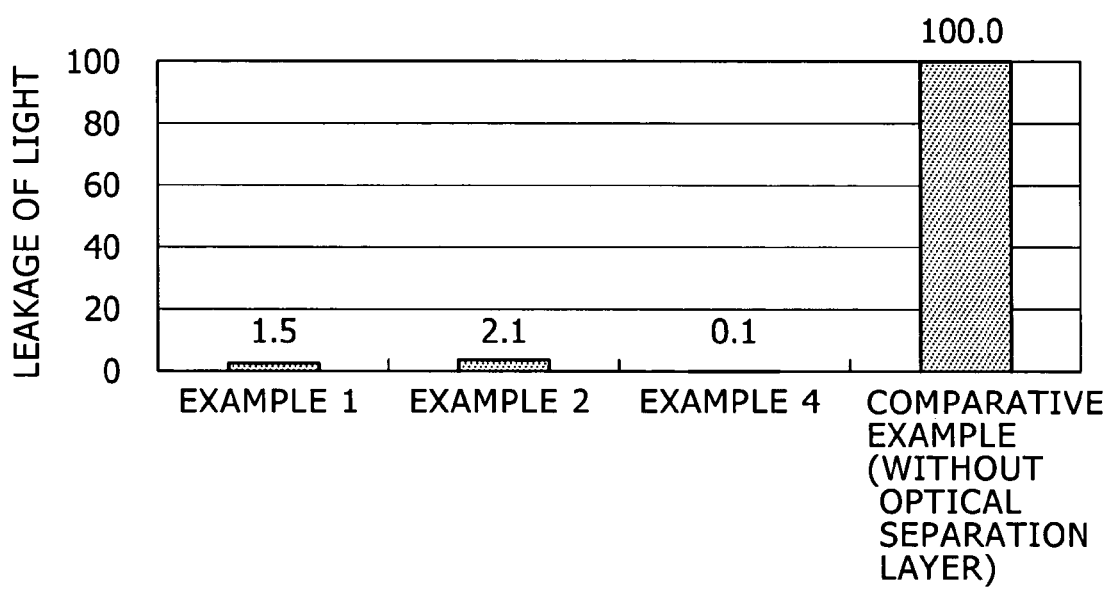
FIG. 10 is a graph showing the results of evaluation of light leakage through the indicator layer.

FIG. 10 is a graph showing the results of evaluation of light leakage in Examples 1 and 2 and Comparative Example. Incidentally, leakage of light was indicated in terms of relative values, wherein the result (measured value) of measurement for the detection layer of Comparative Example lacking the optical separation layer was taken as 100.

As shown in the figure, it is seen that the indicator layers prepared in Examples 1 and 2 showed little light leakage, as compared with Comparative Example lacking the optical separation layer. This shows that, where the indicator layer is used in an embedded-in-body type sensor, the optical separation layer located on the outside thereof can effectively shield light. Therefore, for example, where UV rays or the like is used inside the sensor as the excitation light, the problem that the UV rays would leak out of the sensor to influence the living body tissues can be prevented from occurring. In addition, the problem that light penetrating through the living body tissues would enter into the sensor embedded in the living body to thereby obstruct the fluorescence detection can be prevented from occurring.

Evaluation 3

Evaluation of Time Variation of Indicator Layer

Only the optical separation layer side of the indicator layer was brought into continuous contact with blood plasma containing 100 mg/dl of glucose at 4° C., and the fluorescence intensity was measured along the lapse of time, whereby variation in fluorescence intensity was evaluated.

Figure 11:
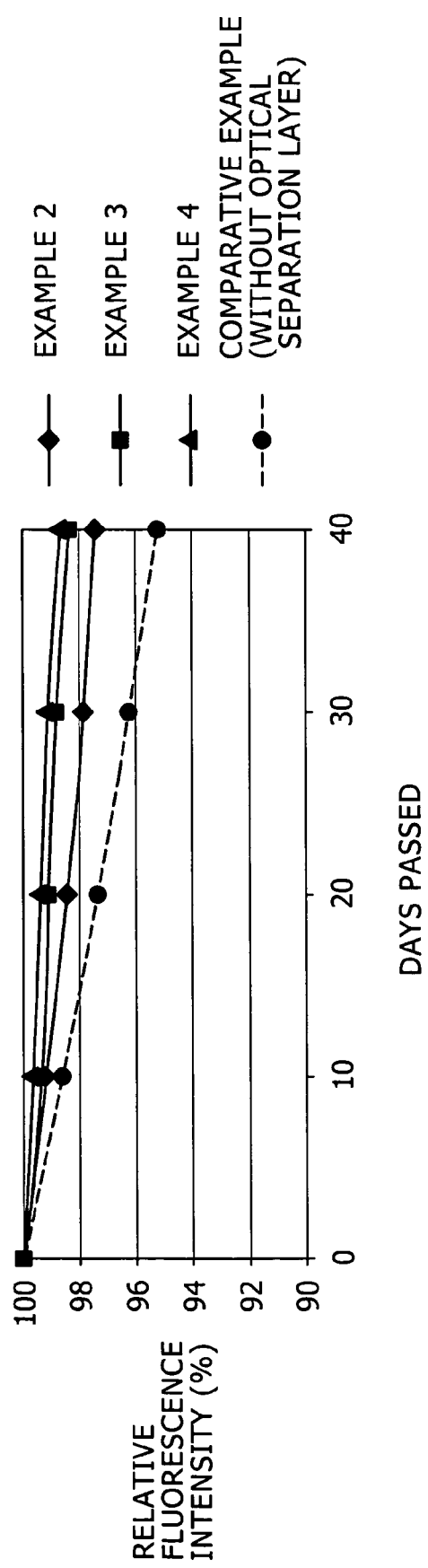
FIG. 11 is a graph showing the results of evaluation of time variation of the indicator layer.

FIG. 11 is a graph showing the evaluation results of time variation of the indicator layers. Incidentally, FIG. 11 is a graph which shows the time variation of relative fluorescence intensity, with the initial fluorescence intensity taken as 100%. Here, an excitation wavelength of 405 nm and a measurement wavelength of 440 nm were used.

It is seen that the indicator layers having the optical separation layer of Examples 2 and 3 showed less reductions in fluorescence intensity with the lapse of time, as compared with the indicator lacking the optical separation layer of Comparative Example. This indicates that the deterioration speeds of the indicator layers having the optical separation layer of Examples 2 and 3 are low.

In addition, it is seen that the indicator layer having the optical separation layer with fullerene as the opaque substance of Example 3 showed less reduction in fluorescence intensity with the lapse of time and, hence, a lower deterioration speed of the indicator layer, as compared with the indicator layer having the optical separation layer with carbon black as the opaque substance.

These results show that the optical separation layer contributes to prevention of deterioration of the detection layer and that fullerene has a higher deterioration-retarding effect than carbon black. This is considered to be a result of the process in which fullerene and carbon black inactivated the deterioration-accelerating substances (for example, radicals) in the blood plasma, whereby decomposition of the fluorescent indicator was restrained.

From the embodiments and examples described above, it is seen that the intracorporeal substance measuring assembly (indicator layer) according to the present invention has a configuration in which an optical separation layer is provided on a detection layer for emitting fluorescence according to an analyte, whereby response to the analyte is enhanced. In addition, since the optical separation layer prevents the living body substances which would obstruct the measurement of the analyte from reaching the detection layer, it is possible to assuredly measure the analyte, to restrain deterioration of the detection layer, particularly the fluorescent indicator therein, and to enable continuous measurement for a long time.

While the embodiments and examples of the present invention have been described above, the present invention is not limited to the embodiments and examples.

For example, while the thin film-shaped body was produced as the indicator in the above examples, the indicator layer is not limited to that shape, and may assume any shape such as rod-like shape and pellet-like shape. In addition, the size and thickness of the indicator layer can be determined freely, according to the purpose of use thereof. In this case, it suffices for the optical separation layer to be provided on the detection layer so that the living body substances will not make direct contact with the detection layer, and the shapes and sizes of the layers can be independently set arbitrarily.

Furthermore, it is natural that the present invention may be variously modified by those skilled in the art, and such modified examples are also embraced in the scope of the technical thought of the present invention.

The objects of the present invention can be attained as follows.

According to the present invention, there is provided an intracorporeal substance measuring assembly provided in an embedded type substance sensor for detecting and measuring an intracorporeal analyte, including: a detection layer containing at least one fluorescent indicator for generating fluorescence according to the concentration of the analyte; and an optical separation layer being provided on one side of the detection layer, being optically opaque, and permitting the analyte to penetrate therethrough.

The detection layer may preferably be comprised of a base material bound to the fluorescent indicator.

Where the analyte is a saccharide, the fluorescent indicator may be a fluorescent substance containing phenylboronic acid.

The fluorescent substance containing phenylboronic acid may preferably be represented by the following chemical formula (1):

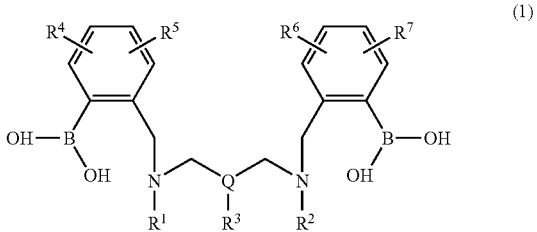

where Q is a fluorescent residual group, at least one of R1, R2, and R3 is an active group to be bound to the base material of the detection layer, R4, R5, R6, and R7 are each at least one substituent group selected from the group consisting of hydrogen atom, alkyl, alkenyl, allyl, allylalkenyl, substituted alkyl, oxyalkyl, acyl, and halogen atom.

In the formula, Q may be a fluorescent residual group containing anthracene.

The base material of the detection layer may preferably be a light-transmitting polymeric substance.

The polymeric substance may be at least one polymeric substance selected from the group consisting of cellulose, polyacrylamide, polyethylene glycol, polyvinyl alcohol, and derivatives thereof.

The optical separation layer may be composed of an opaque substance and a base material for supporting the opaque substance.

The opaque substance may preferably be composed of at least one substance selected from the group consisting of carbon black, fullerene, and carbon nanotube.

The base material of the optical separation layer may be a polymeric substance.

The polymeric substance may preferably be cross-linked dextran.

The optical separation layer may be a polymeric porous film formed by a phase transition method.

The polymeric porous film is preferably composed of at least one of cellulose derivatives, polysulfone-based reins, polyamide-based resins, and aromatic polyether-ketone resins.

Preferably, the optical separation layer may permit the analyte to penetrate therethrough, and may not permit at least one intracorporeal component other than the analyte to penetrate therethrough.

The optical separation layer may have biocompatibility.

The optical separation layer preferably may not permit intracorporeal components deteriorating the detection layer to penetrate therethrough.

Preferably, the optical separation layer may inactivate the intracorporeal components.

Further, in accordance with the present invention, there is provided a method of producing an intracorporeal substance measuring assembly as above-mentioned, including the steps of adding to the detection layer a precursor for forming the optical separation layer, and thereafter binding the precursor to the detection layer.

Furthermore, in accordance with the present invention, there is provided a method of producing an intracorporeal substance measuring assembly as above-mentioned, including the step of adding a peripheral portion of the optical separation layer to the periphery of the detection layer.

In accordance with the present invention, there is provided an embedded type substance sensor including: an intracorporeal substance measuring assembly as above-mentioned; a light source for irradiating the detection layer with light from the detection layer side of the intracorporeal substance measuring assembly; and a photo-detector for receiving fluorescence from the detection layer.

Preferably, the embedded type substance sensor may be used in the condition where the optical separation layer side of the intracorporeal substance measuring assembly is in contact with a living body.

Preferably, at least the light source and the photo-detector may be provided in the same package so that the optical separation layer side of the intracorporeal substance measuring assembly is exposed from the outside surface of the package.

Preferably, the light source may emit at least one kind of wavelength, and the photo-detector may detect light having at least one wavelength from the detection layer.

What is claimed is:

1. An intracorporeal substance measuring assembly provided in an embedded type substance sensor for detecting and measuring an intracorporeal analyte, comprising:
   a detection layer containing at least one fluorescent indicator containing phenyl boronic acid that generates fluorescence according to the concentration of said analyte; and
   an optical separation layer on one side of said detection layer that is optically opaque and permits said analyte to penetrate therethrough;
   wherein said analyte is a saccharide, and said fluorescent indicator is represented by formula (1):

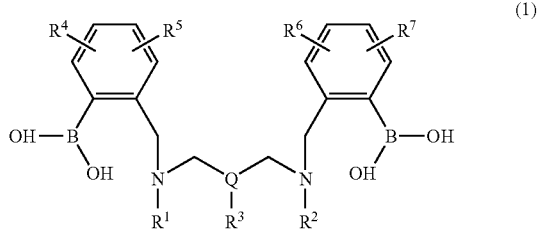

where Q is a fluorescent residual group; at least one of R1, R2, and R3 is an active group bound to a base material of said detection layer; R4, R5, R6, and R7 are each at least one substituent group selected from the group consisting of hydrogen atom, alkyl, alkenyl, allyl, allylalkenyl, substituted alkyl, oxyalkyl, acyl, and halogen atom.

2. The intracorporeal substance measuring assembly as set forth in claim 1, wherein Q is a fluorescent residual group containing anthracene.

3. The intracorporeal substance measuring assembly as set forth in claim 1, wherein said optical separation layer is comprised of an opaque substance and a base material for supporting said opaque substance.

4. The intracorporeal substance measuring assembly as set forth in claim 3, wherein said opaque substance is comprised of at least one substance selected from the group consisting of carbon black, fullerene, and carbon nanotube.

5. The intracorporeal substance measuring assembly as set forth in claim 1, wherein said optical separation layer is a polymeric porous film formed by a phase transition method.

6. The intracorporeal substance measuring assembly as set forth in claim 1, wherein said optical separation layer does not permit intracorporeal components that deteriorate said detection layer to penetrate therethrough.

7. The intracorporeal substance measuring assembly as set forth in claim 6, wherein said optical separation layer inactivates said intracorporeal components.

8. A method of producing an intracorporeal substance measuring assembly provided in an embedded type substance sensor for detecting and measuring an intracorporeal saccharide analyte the method comprising: providing a detection layer containing at least one phenyl boronic acid-containing fluorescent indicator that fluoresces according to the concentration of said analyte; and an optical separation layer disposed on one side of said detection layer that is optically opaque and permits said analyte to penetrate therethrough, wherein said fluorescent indicator is represented by formula (1):

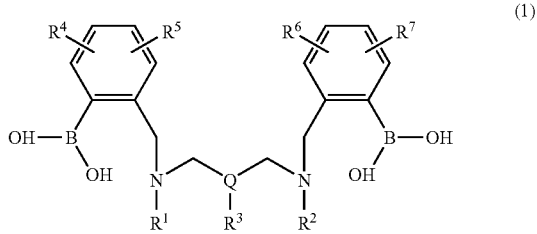

(1)

where Q is a fluorescent residual group: at least one of R1, R2, and R3 is an active group to be bound to said base material of said detection layer: R4, R5, R6, and R7 are each at least one substituent group selected from the group consisting of hydrogen atom, alkyl, alkenyl, allyl, allylalkenyl, substituted alkyl, oxyalkyl, acyl, and halogen atom;

binding the at least one active group to said base material; and adding to said detection layer a precursor for forming said optical separation layer, and thereafter binding said precursor to said detection layer.

9. A method of producing an intracorporeal substance measuring assembly provided in an embedded type substance sensor for detecting and measuring an intracorporeal saccharide analyte the method comprising: providing a detection layer containing at least one phenyl boronic acid-containing fluorescent indicator that fluoresces according to the concentration of said analyte; and an optical separation layer disposed on one side of said detection layer that is optically opaque, and permits said analyte to penetrate therethrough, wherein said fluorescent indicator is represented by formula (1):

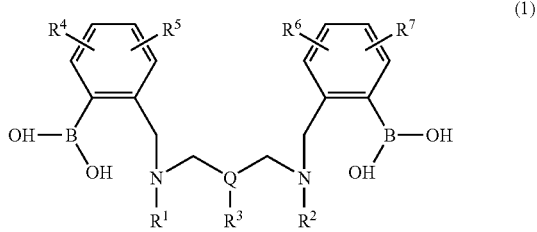

(1)

where Q is a fluorescent residual group: at least one of R1, R2, and R3 is an active group to be bound to said base material of said detection layer: R4, R5, R6, and R7 are each at least one substituent group selected from the group consisting of hydrogen atom, alkyl, alkenyl, allyl, allylalkenyl, substituted alkyl, oxyalkyl, acyl, and halogen atom;

binding the at least one active group to said base material; and adhering a peripheral portion of said optical separation layer to the periphery of said detection layer.

10. An embedded type substance sensor comprising:

an intracorporeal substance measuring assembly provided in an embedded type substance sensor for detecting and measuring an intracorporeal saccharide analyte including: a detection layer containing at least one phenyl boronic acid-containing fluorescent indicator that fluoresces according to the concentration of said analyte, wherein said fluorescent indicator is represented by formula (1):

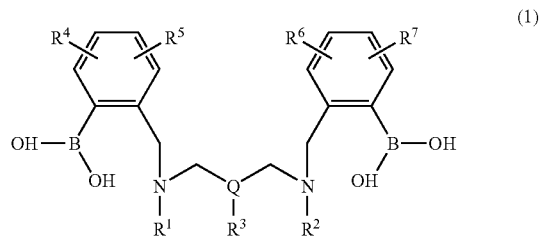

(1)

where Q is a fluorescent residual group; at least one of R1, R2, and R3 is an active group bound to a base material of said detection layer; R4, R5, R6, and R7 are each at least one substituent group selected from the group consisting of hydrogen atom, alkyl, alkenyl, allyl, allylalkenyl, substituted alkyl, oxyalkyl, acyl, and halogen atom;

and an optical separation layer disposed on one side of said detection layer that is optically opaque, and permits said analyte to penetrate therethrough;

a light source oriented to irradiate said detection layer from the detection layer side of said intracorporeal substance measuring assembly; and a photo-detector oriented to detect fluorescence from said detection layer.

11. The embedded type substance sensor as set forth in claim 10 wherein the optical layer side of said intracorporeal substance measuring assembly is configured to be in contact with a living body.

* * * * *